United States Patent [19]

Warner et al.

[11] Patent Number: 5,643,286

[45] Date of Patent: Jul. 1, 1997

[54] MICRODRIVE FOR USE IN STEREOTACTIC SURGERY

[75] Inventors: Nicholas Warner, Belmont, Mass.; Moses Goddard, Tiverton; John Mills, Wakefield, both of R.I.

[73] Assignee: CytoTherapeutics, Inc., Providence, R.I.

[21] Appl. No.: 265,242

[22] Filed: Jun. 24, 1994

[51] Int. Cl.⁶ .............................. A61B 19/00; A61B 17/56
[52] U.S. Cl. .............................. 606/130; 606/96; 606/98; 606/167; 606/172; 604/116
[58] Field of Search .............................. 606/1, 130, 108, 606/96–98, 129, 167, 172; 128/749, 653.1, 653.2; 604/116

[56] References Cited

U.S. PATENT DOCUMENTS

| | | | |
|---|---|---|---|
| 3,223,087 | 12/1965 | Vladyka et al. | 606/129 |
| 3,817,249 | 6/1974 | Nicholson | 606/130 |
| 4,653,509 | 3/1987 | Oloff et al. | 606/130 X |
| 4,722,336 | 2/1988 | Kim et al. | 606/130 |
| 4,750,487 | 6/1988 | Zanetti | 606/130 |
| 4,875,478 | 10/1989 | Chen | 606/130 X |
| 4,940,061 | 7/1990 | Terwillerger. | |
| 5,056,523 | 10/1991 | Hutchkiss, Jr. et al. | 606/130 X |
| 5,080,662 | 1/1992 | Paul | 606/130 |
| 5,154,723 | 10/1992 | Kubota et al. | 606/130 |
| 5,183,465 | 2/1993 | Xanthakos et al. | 606/172 X |
| 5,308,352 | 5/1994 | Koutrouvelis | 606/130 |

FOREIGN PATENT DOCUMENTS

| | | | |
|---|---|---|---|
| 2584601 | 1/1987 | France. | |
| 869842 | 3/1953 | Germany. | |
| 1055503 | 11/1983 | U.S.S.R. | 606/130 |

OTHER PUBLICATIONS

Bland et al., "A Direct–Drive, Non–Rotating Version of Ranck's Microdrive", *Physiology and Behavior*, vol. 24, May 16, 1979, pp. 395–397.

*Primary Examiner*—Danton D. DeMille
*Attorney, Agent, or Firm*—Ivor Elrifi; Bruce F. Jacobs

[57] ABSTRACT

The present invention is directed to microdrive apparatus useful in human stereotactic surgery. Such apparatus permits safe and accurate placement of a surgical instrument, such as a cannula, into a portion of the central nervous system, e.g. the brain and spinal cord, of a patient by simple mechanical operation.

12 Claims, 6 Drawing Sheets

MICRODRIVE FOR USE IN STEREOTACTIC SURGERY

BACKGROUND OF THE INVENTION

Stereotactic surgery is that branch of neurosurgery that uses a special device to direct a surgical instrument such as a cannula, electrode or other type of probe or device, with great accuracy, to a target within the central nervous system, particularly the brain or spinal cord, of a patient. The target is located and identified by one of a number of techniques. Sometimes the target can be visualized on computed tomography (CT) or magnetic resonance imaging (MRI). Other times, the position of the target must be determined by its relationship to an anatomic structure that can be seen on scanning using conventional radiographs or by ventriculography. Today, three-dimensional imaging techniques such as CT and MRI are the most frequently used techniques to locate and identify targets within the central nervous system.

Stereotactic surgery can only be carried out using a special apparatus which enables the surgeon to guide surgical instruments to identified targets within the brain, spinal cord, or other part of the central nervous system. There are several such devices in use today ranging from custom designed devices to commercially available devices. Most stereotactic devices have several things in common. The devices are attached securely to the patient, generally the head, the exact three-dimensional spatial relationship between the target and the device is determined after visualization of the target by an x-ray or imaging technique, and the device has a probe or instrument holder that can be adjusted to advance an instrument from various directions to the target with great accuracy. A particularly accurate instrument holder is known as a microdrive which is used by a surgeon to accurately advance a surgical instrument to a predetermined target in the brain.

The commonly used and/or known stereotactic apparati are the Leksell apparatus, the Riechert-Mundinger Apparatus, the Todd-Wells apparatus and the Brown-Roberts-Wells apparatus. The Leksell apparatus is a target-centered device utilizing a 19 cm radius arc and traveler arrangement to guide a surgical instrument to the target. The traveler arrangement may be a microdrive. The entire apparatus is generally attached to the patient's head using a metal frame.

The Ricchert-Mundinger apparatus is a polar coordinate device with two movable arcs allowing motion of the probe holder such as a microdrive in three dimensions. Once aligned with target point-entry point vector, the probe length need only be determined for the proper distance to reach the target point.

Like the Leksell apparatus, the Todd-Wells apparatus is a target-centered device in which the target point is placed at the center of an adjustable radial coordinate system. The Todd-Wells apparatus differs from the Leksell apparatus in that it is the head which is moved to align the target point, not the frame.

The Brown-Robert-Wells apparatus was the first device created for use with CT. The apparatus established the concept of frame-centered sterotoxy, operating in such a manner so that the target need not be moved to the center of some arc. This was possible by making use of the three-dimensional information in the CT images to establish a three-dimensional vector of entry point to target point. The frame is then adjusted by moving four rotational settings so that the probe holder aligns with the entry-target vector.

A variety of instruments may be used with any of these or other stereotactic devices including electrodes, cannulas, biopsy instruments, catheters and the like.

A particularly preferred type of probe or instrument holder is a microdrive which attaches to and forms a part of the stereotactic apparatus to provide the capability of accurately guiding and directing a surgical instrument to a target. A microdrive, as opposed to other stereotactic instrument holders is an instrument holder which includes means to accomplish a controlled advancement of a medical instrument.

In use, a 0 point or reference point is determined by an appropriate technique such as CT or MRI and the target point within the brain is calculated in reference to the 0 point. Then, the stereotactic head assembly is adjusted and the instrument holder or microdrive is set with reference to the 0 point. A surgical instrument is then ready to be advanced into the brain.

Many microdrive devices have been developed for use in laboratory animals. For example, Bland et al, "A Direct-Drive, Non-Rotating version of Ranck's Microdrive," *Physiology & Behavior*, Vol. 24, pp. 395–397 (1990) describes a direct drive, non-rotating microdrive for the implantation of microelectrodes for the measurement of extra cellular unit potentials in freely moving animals. Bland's microdrive utilizes a headed stainless steel screw to move an electrode into a desired location within the animal's brain. This microdrive has only a very limited advancement range and is not adapted for stereotactic frames suitable for human use.

Radionics (Burlington, Mass.) is the only supplier of current commercially available microdrives suitable for use in human subjects. The Radionics® microdrive utilizes a gear assembly to achieve depth placement. There are inherent drawbacks to such an approach. First, actuating the gear mechanism causes undesirable vibration along the instrument, which could result in vibration of the implement being lowered into the burr hole; e.g., a cannula. This can result in undesirable tissue damage. In addition, the mechanical engagement of the gear teeth may cause some debris to flake off the instrument, potentially contaminating the operation site. Further, some surgeons have found that the instrument tends to "free fall," which could cause sudden, uncontrolled movement of the cannula into the brain of the patient.

U.S. Pat. Nos. 5,004,457 and 5,006,122 disclose tissue implantation systems which utilize a conventional instrument holder available from David Kopf Instruments (Tujanga, Calif.).

Accordingly, there is a need for a microdrive which will provide easy setting of zero points with reference to a patient's scalp, skull, or dura, as the case may be. In addition, there is a need for a microdrive which can also capture a pusher which is often used to hold an implant in position while a cannula or other instrument is being removed from a target.

It is an object of the present invention to develop a microdrive that overcomes the disadvantages of the prior art microdrives and which is useful with a variety of stereotactic devices used for human surgery.

DISCLOSURE OF THE INVENTION

The present invention is directed to a novel microdrive apparatus. As used herein the term "microdrive apparatus" means an apparatus useful with a stereotactic assembly or equivalent apparatus to hold and direct a surgical instrument into a target which is a portion of the central nervous system of a patient. Preferably, the stereotactic assembly is a head ring and the target is in the brain. The microdrive apparatus generally comprises a base member, an elongated guide member fixedly attached to the base member, an instrument holding member slidably attached to the guide member having a means for holding a surgical instrument, a stop member slidably attached to the guide member and disposed between the base member and the instrument holding member. The stop member has a measuring member containing measuring indicia thereon fixedly attached thereto. The instrument holding member is attached to the guide member in a manner that prevents its movement and the movement of a surgical instrument attached thereto in any direction except along the longitudinal axis of the guide member. This is an important feature of the present invention since movement in other directions, even slight movement, could have detrimental to the surgery being performed. The instrument holding member is preferably designed for use with a specific instrument; e.g., a cannula. The cannula advanced by the microdrive is most preferably used as an implantation device for a NeuroCRIB® device available from CytoTherapeutic Inc. The instrument holding member is interchangeable with other such members, depending on the specific instrument to be used with it.

The microdrive apparatus may be used with most of the variety of stereotactic assemblies used in stereotactic surgery. In use, the microdrive is attached to the stereotactic assembly via its base and particularly the adapter portion of the base. Depending upon the stereotactic assembly being used, the adapter portion of the base may either have to be designed to facilitate attachment or an adapter sleeve must be attached thereto to allow for attachment. The use of interchangeable instrument holding members enables the microdrive of the present invention to be used with any of the surgical instruments used in stereotactic surgery. In any case, the general operation of the microdrive apparatus remains the same. It facilitates the insertion of surgical instruments into the central nervous system, e.g. the brain or spinal cord, with accuracy, safety and by means of a simple mechanical operation.

DETAILED DESCRIPTION OF THE PREFERRED EMBODIMENTS

The microdrive apparatus of the present invention will now be described with reference to the drawings. The embodiment shown in FIGS. 1-6 describes one apparatus according to the present invention which is particularly useful in inserting a cannula into the brain, through which cannula an implant may be inserted. While this embodiment describes a microdrive which is particularly suited for cannula insertion into the brain, it should be understood that the basic structure, design and operation of the apparatus is the same for whatever surgical instrument is being inserted and whatever instrument holding member is being used.

Figure 1:
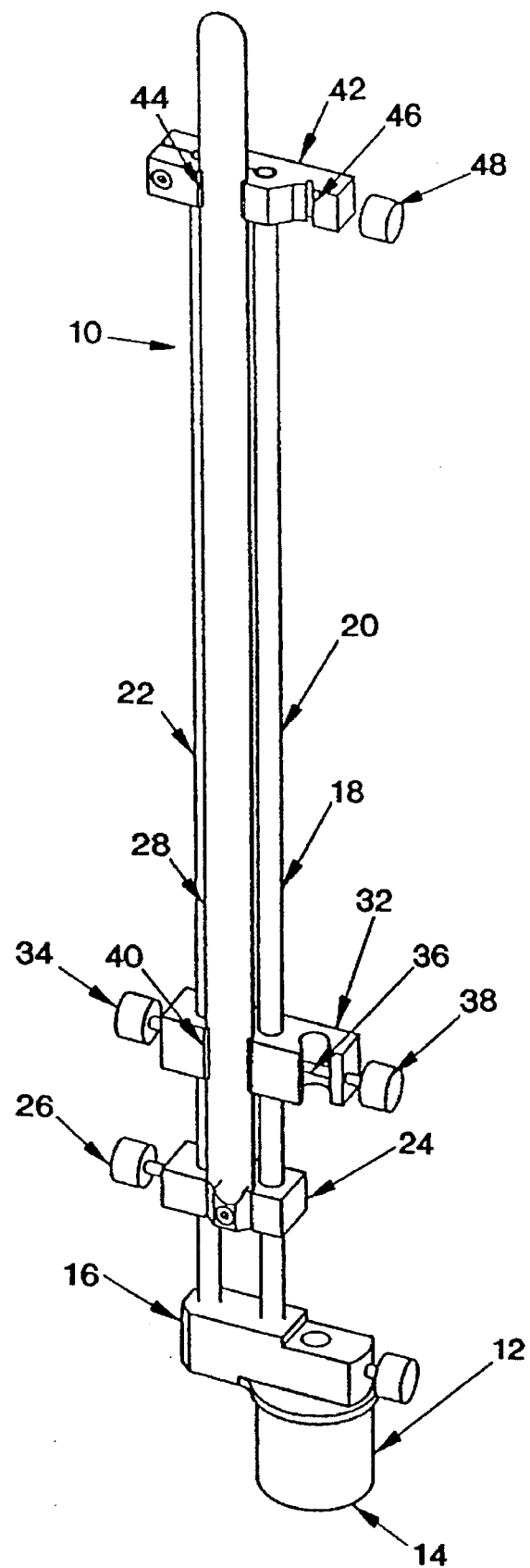
FIG. 1 is a front perspective view of an embodiment of the present invention.
Figure 2:
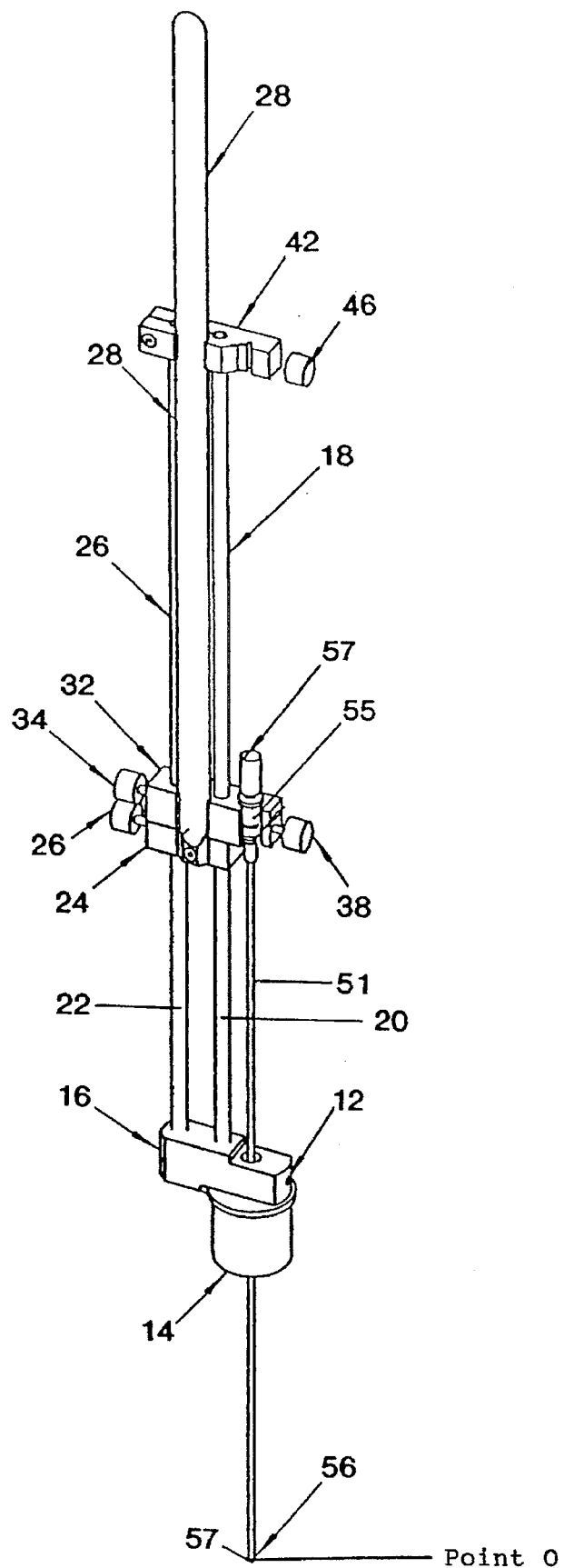
FIGS. 2-4 are front perspective views of the embodiment of FIG. 1 at different stages of use.
Figure 3:
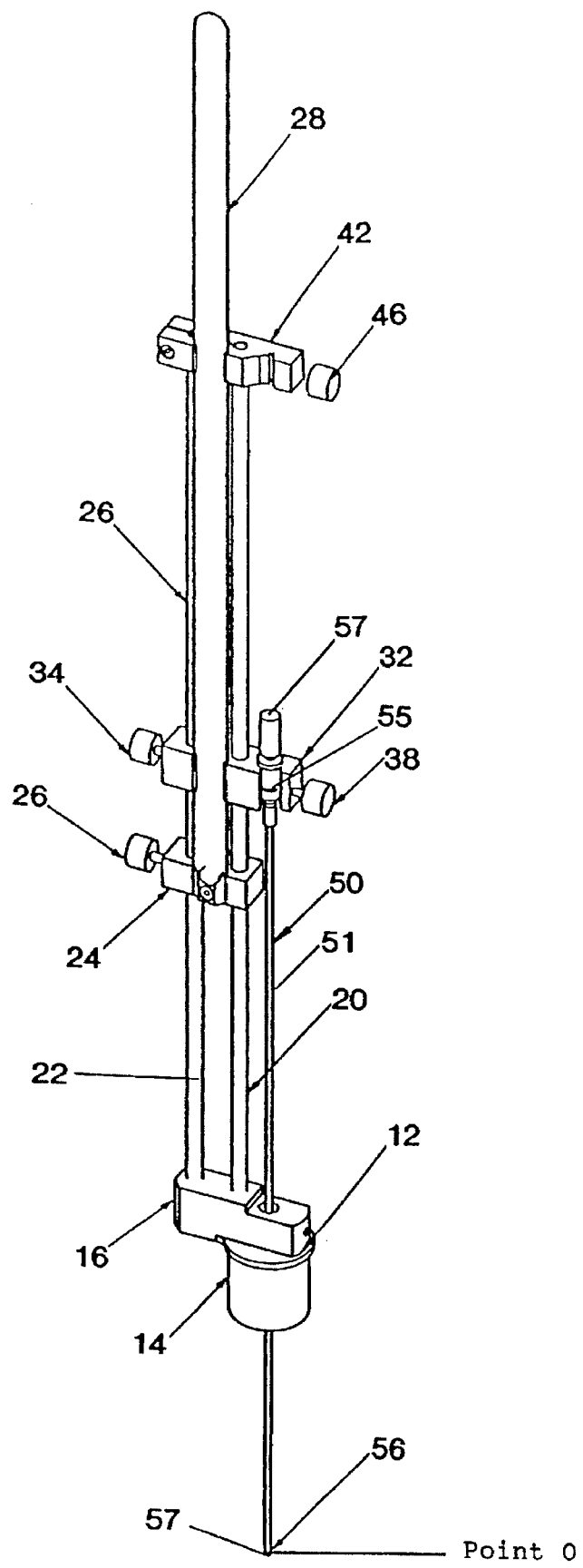
Figure 4:
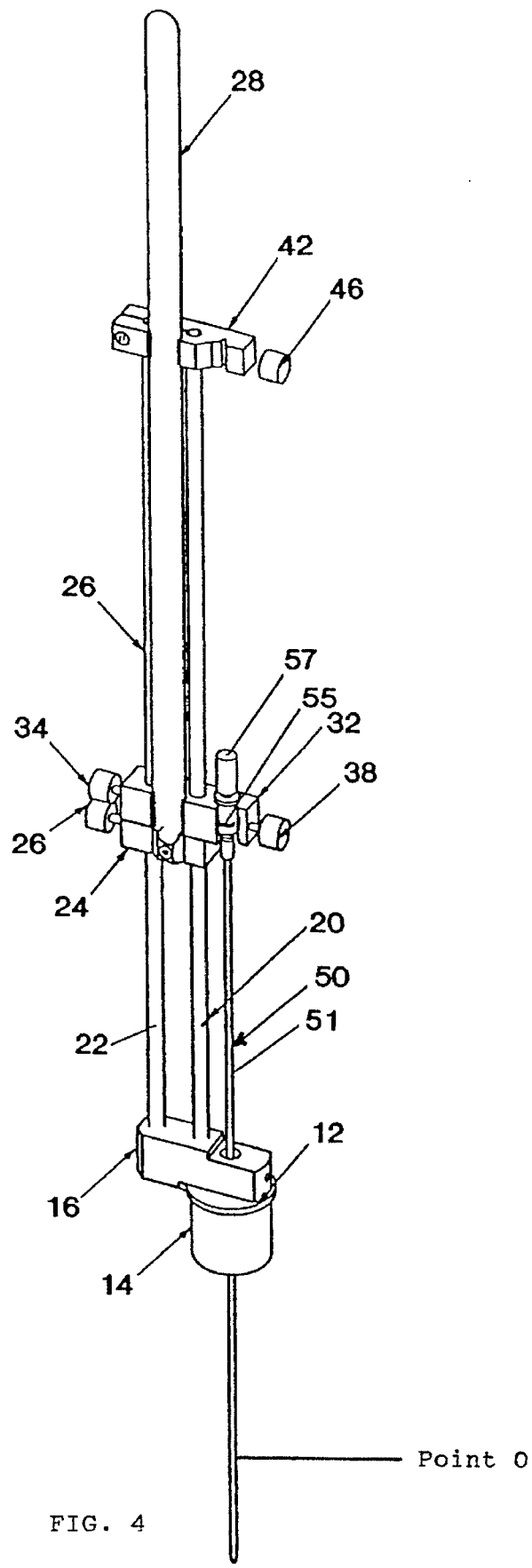
Figure 5:
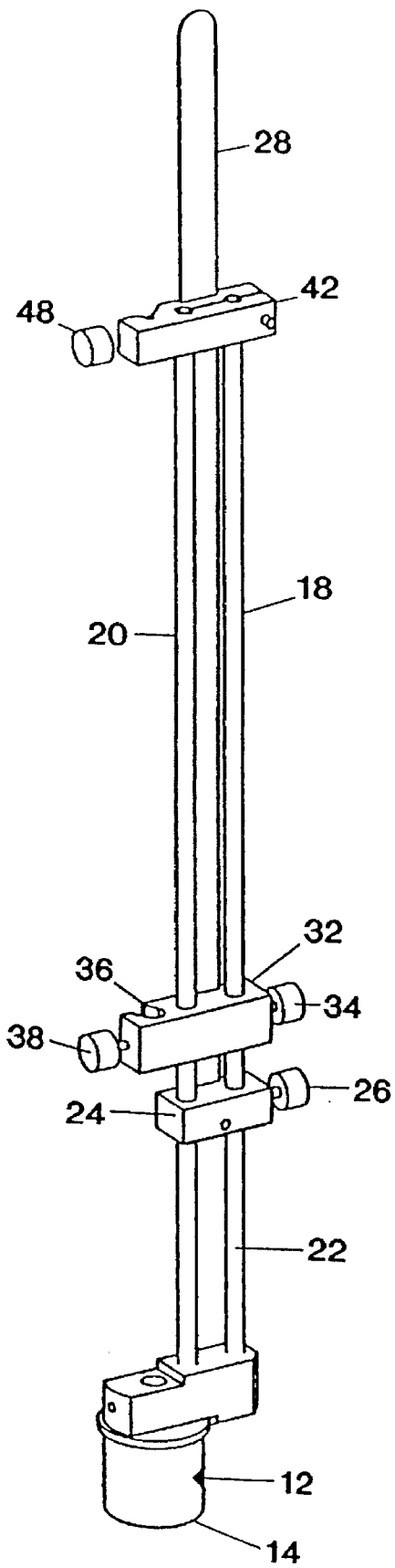
FIG. 5 is a rear perspective view of the embodiment of FIG. 1.

Referring to FIG. 1, a microdrive 10 of the present invention comprises a base member 12 having an adapter base portion 14 and a base stop portion 16. As shown, the two portions of the base member are integral therewith. However, they may be separate members fixedly attached to each other. The base member 12 has a channel which extends therethrough so that a surgical instrument which is attached to the instrument holder can pass therethrough in use. The channel is best shown in FIGS. 2-4. The base member as shown in FIG. 1 is designed for use with the Radionics® BRW head frame assembly. For use with other head assemblies, other adapter bases (the shape and size of which are readily determinable from measurements of the mounting block of the particular stereotactic frame being used) or an adapter sleeve may be used. Attached to the base member 12 is a guide member shown generally as 18. The guide member in this embodiment is composed of two elongated cylindrical rods 20 and 22 which are fixedly attached to the base member 12.

Stop member 24 containing a screw clamp 25 is slidably attached to guide member 18. The slidable attachment is achieved by means of two channels which pass through the stop member through which the rods 20 and 22 pass. As a result, the stop member is able to slide up and down along the longitudinal axis of the guide member. The stop member 24 may be temporarily fixedly attached to the guide member 18 by tightening the screw 26 against rod 22. Fixedly attached to the stop member 24 is a measuring member 28, which contains measuring indicia 30 thereon. Such measuring member is generally in the form of a ruler with an appropriate scale and measuring indicia corresponding thereto. Preferably, the scale is a conventional metric scale. In use, as the stop member slides up and down the guide member 18, the measuring member follows.

Instrument holding member 32 is likewise slidably attached to the guide member 18. Like the stop member 24, the instrument holding member 32 has two channels through which the rods 20 and 22 pass. This arrangement permits movement of the instrument holding member along the longitudinal axis of the guide member 18, but prevents movement in any other direction. Again, like the stop member 24, the instrument holding member may be temporarily fixedly attached to the guide member 18 by tightening screw 34 against rod 22. The instrument holding member 32 contains a notch 36 for holding a cannula which may be held in place by a screw 38. As shown, the measuring member 28 is disposed so that it may slide through a notch 40 in instrument holding member 32. This permits unrestricted movement of the stop member 24 relative to the instrument holding member 32.

Figure 6:
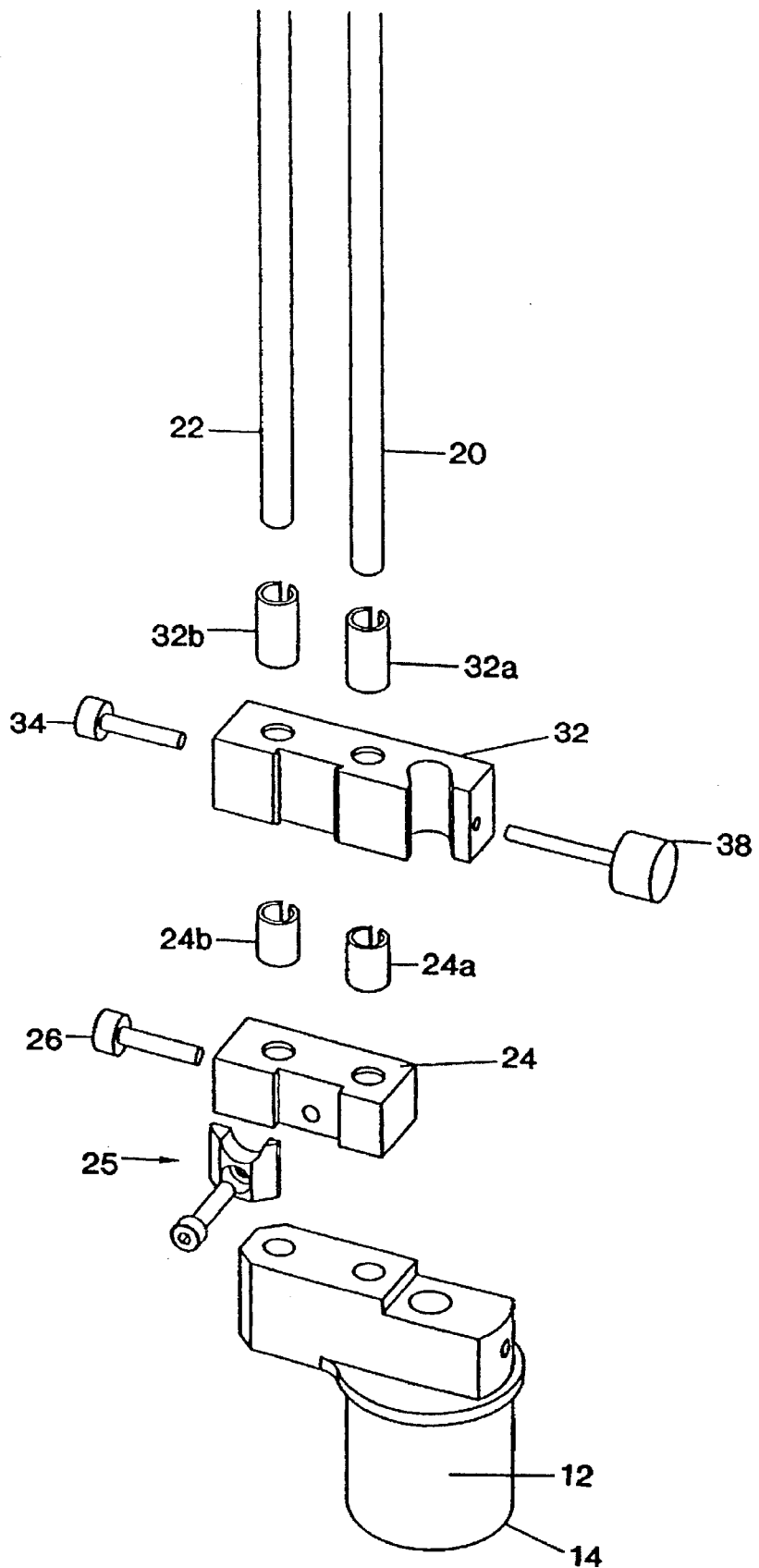
FIG. 6 is an exploded front view of the lower portion of the embodiment of FIG. 1.
Figure 4:
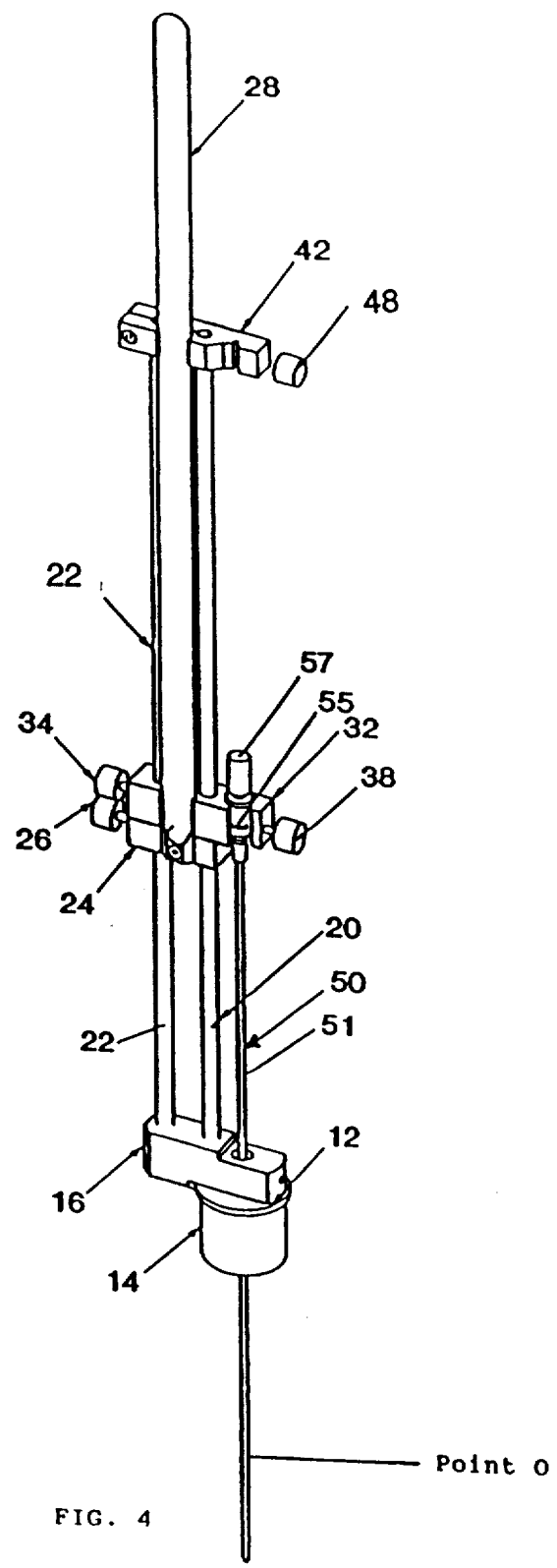
Figure 3:
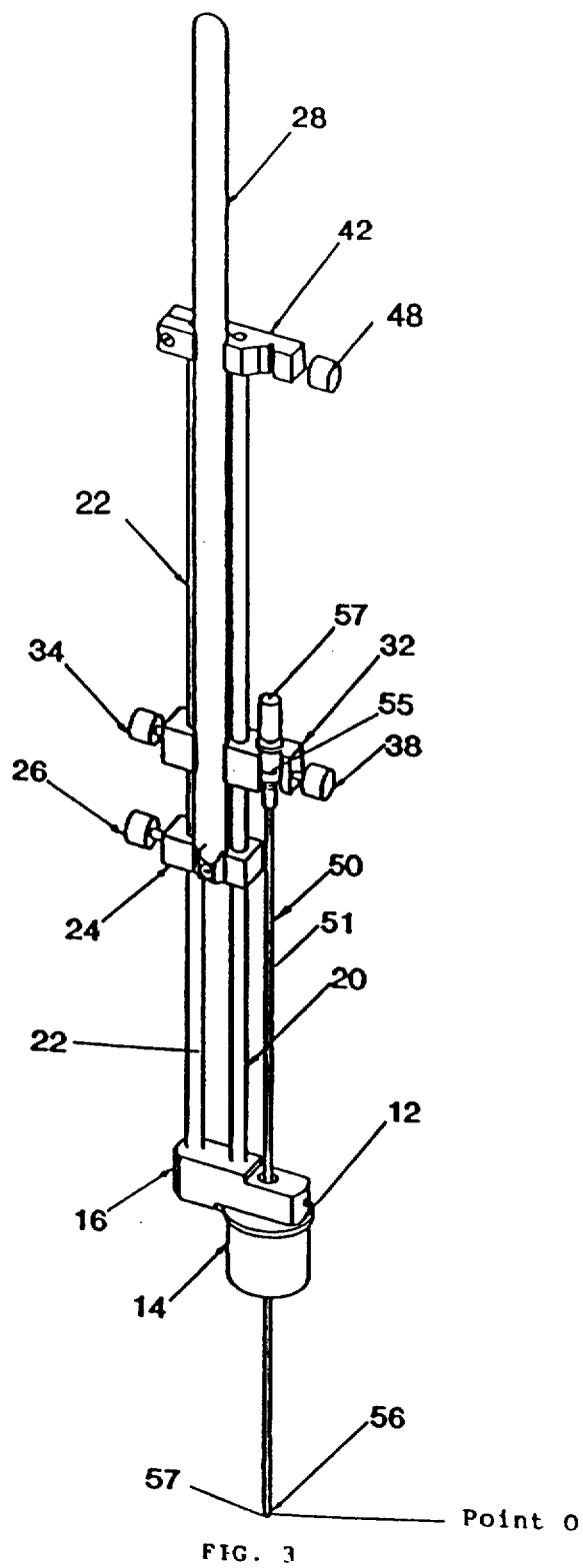
Figure 2:
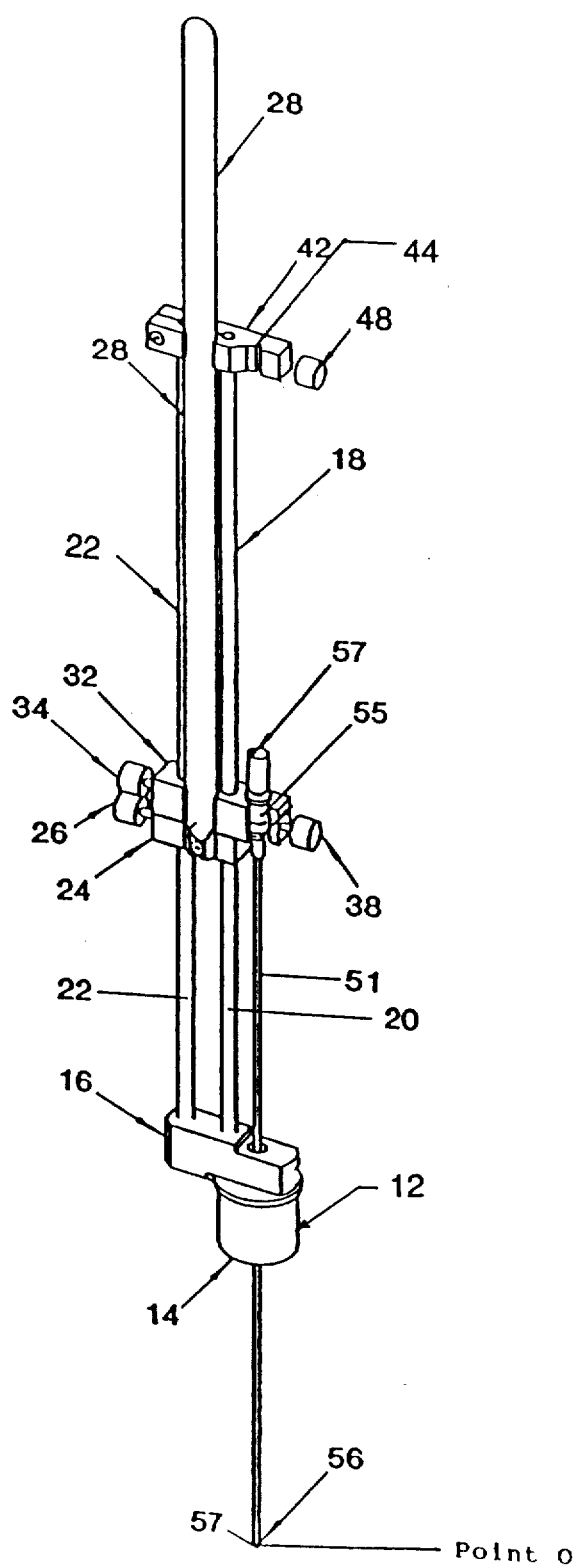
Figure 1:
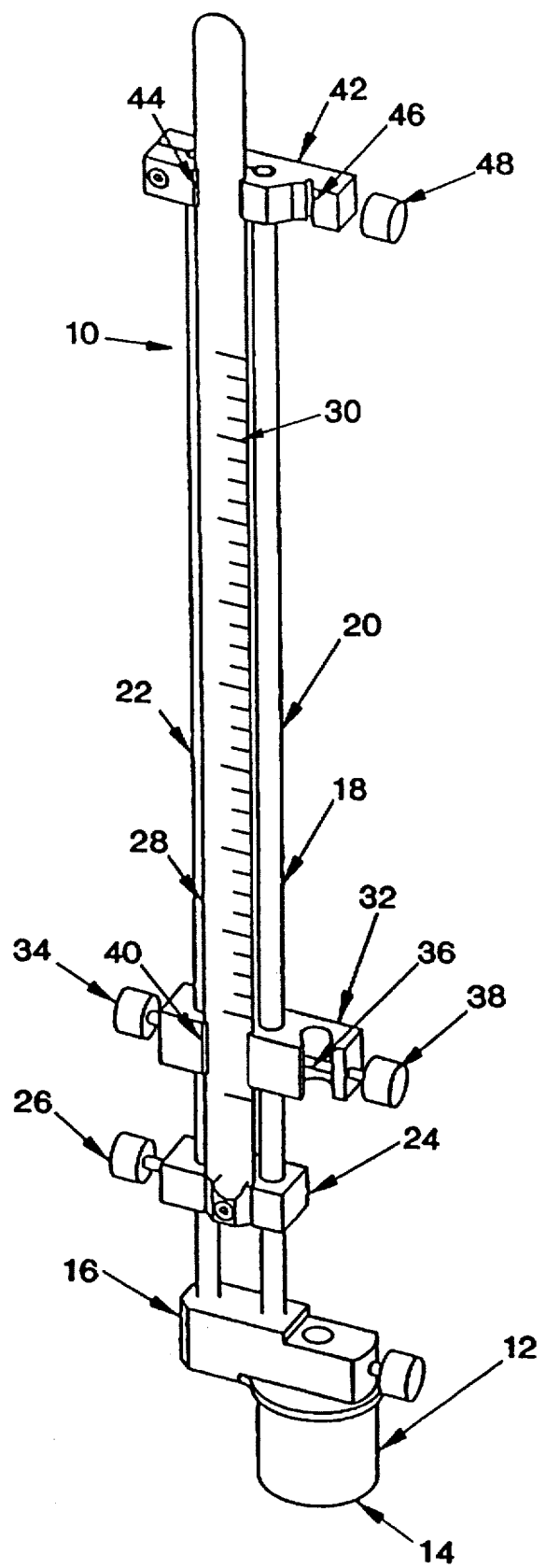

As best shown in FIG. 6, the channels in each of the stop member 24 and the instrument holding member 32 preferably contain means to maintain sufficient pressure to hold the members 24 and 32 in place until intentionally changed. Suitable such means include bushings 24a, 24b, 32a, and 32b, although other means (not shown) such as leaf springs, jack screws, or captured sliders may be used. Preferably the means are bushings which are generally made from or at least coated with a low friction material such as Teflon® or Rulon® material. The bushings or other means allow the stop member and the instrument holding member to ride smoothly along the rods 20 and 22, which are in contact with the bushings, in response to external pressure (surgeon's manipulations) while substantially holding the members 24 and 32 in place when no pressure is being applied. This keeps the members 24 and 32 from suddenly crashing down and causing the instrument to "free fall".

While not necessary for the operation of the microdrive of the present invention, this embodiment shows a second instrument holding member 42 which is fixedly attached to the distal end of the guide member 18. Like instrument holding member 32, the second instrument holding member 42 has a notch 44 which permits the measuring member 28 to slide therethrough. The second instrument holding member also has a notch 46 with a screw 48 for holding an instrument.

In general use a cannula will be inserted into the first instrument holding member 32 with an obturator in place inside the cannula. The obturator serves to part tissue, keep the cannula from scoring tissue, and keep the cannula substantially rigid during insertion. The obturator may or may not be imageable. The second instrument holding member 42 can then hold a pusher with an implant mounted on the end or another instrument (not shown in the drawings). After the obturator has been removed from the cannula, an implant or other instrument may be fed into the cannula and the top of the pusher may be locked into the second instrument holder. Alternatively, the implant or other instrument can simply be inserted into the cannula without use of the holding member 42.

All of the elements of the microdrive should be made of materials which are sterilizable by common methods, including both gas and autoclave means. The materials are rigid and preferably light weight. Thus, for example, the rods 20 and 22 which comprise the guide member 18 can be made of such as graphite reinforced composite or a metal such as stainless steel. The base member 12, the stop member 24, and the instrument holding members 32 and 42 can be made of aluminum, titanium, stainless steel, or high temperature resistant plastics.

In other embodiments according to the present invention the instrument holding member 32 is interchanged with other instrument holding members with slightly different means suitable for holding surgical instruments other than cannulas. Such surgical instruments include electrodes, biopsy instruments, etc.

The operation of the microdrive apparatus of the present invention can best be described with reference to FIGS. 2–4. While the discussion will be with reference to cannula insertion into a brain, it should be understood that the operation of the apparatus which holds another surgical instrument for insertion into other portions of the central nervous system is substantially the same.

As previously discussed in the Background of the Invention section, the target point and a 0 point are established by any of a number of techniques, such as CT and MRI. Once a 0 point is established relative to the target point within the brain, the necessary adjustments are made with the stereotactic head assembly and the necessary hole or holes are drilled through the patients skull down to the dura. Although not shown, the microdrive is attached to a head assembly at this point in the surgical procedure and oriented in the appropriate direction to facilitate surgical instrument placement in the brain.

As shown in FIG. 2, the instrument holding member 32 holds a cannula 50 having a stem 51 in place. Within the cannula is an obturator having a top portion 57 which extends to the tip of the cannula 56 with the obturator's tip 57 extending just beyond the tip of the cannula 56. The cannula generally includes a conventional luer style taper lock 55 to maintain the obturator in place. The stop member 24 and the instrument holding member are then held together and adjusted on the guide member 18 to a position so that the obturator tip 57 is at the 0 point, e.g. the skin of the scalp of the patient. Once the two members are adjusted to the 0 point position, both members are temporarily held in place by tightening screws 26 and 34 against the rod 26. Then, as shown in FIG. 3, the screw on the stop member is loosened and it is moved downward or towards the base a predetermined distance equal to the pre-measured distance to the target from point 0. This distance is easily determined using the measuring member 28 and the scale printed thereon. In the embodiment shown in FIG. 4, this distance is identified as 5 mm, although the drawings are not to scale. Once the stop member 24 reaches this position, it is again held in place by tightening screw 26. Then, as best shown in FIG. 4, the screw 38 is loosened and the instrument holding member is moved towards the base member 12 until it is stopped by stop member 24. In turn, the cannula with obturator therein is inserted into the brain the premeasured distance (in this case 5 mm) to the target point. Screw 34 is then tightened preventing movement in any direction of the instrument holding member 32 or cannula 50. Now that the cannula tip is at the target point, the obturator may be removed and other surgical devices may be lowered through the cannula into the brain, such as an implant device, and held in place by means of the second instrument holding member 42 and screw 46.

Whether a cannula or some other instrument is used, the general operation of the microdrive is the same excepting the need and use of the second instrument holding member 42 which is only needed when a second surgical instrument is used. An example of an alternative second instrument is a single action biopsy forceps such as that designed for use with the Leksell Stereotactic Instrument.

A particularly suitable implantation therapy system and method for so doing are disclosed in copending application U.S. Ser. No. 07/998,368, Aebischer et al, entitled "Implantable Therapy Systems and Methods," filed Dec. 30, 1992, (Attorney Docket No. CTE-018), the subject matter of which is incorporated herein by reference.

EXAMPLE

Closed, cannula based, stereotactic implantation technique for placement of encapsulated cellular grafts intracranially in the lateral ventricle in a human Immediately before an implantation procedure, a patient was fitted with a stereotactic head ring assembly and localizer ring (or image localization/marker device) suitable for guided cannula placement within the lateral ventricles using local anesthesia (local infiltration with generally 1% lidocaine). The Radioinics® BRW frame was used. (The Radionics® CRW, Leksell® and functionally similar devices are also appropriate.) A computed tomography (CT) scan had been performed and was used to define one or more target sites and stereotactic coordinates for the implant(s). In general, implantation cannula trajectory and implant site are chosen with the following considerations: (1) avoiding the frontal sinuses; (2) avoiding the choroid plexus; and (3) allowing straight, undistorted positioning capsule lengths 2.5, 3.75, or 5.0 cm). A target site must be selected that will allow a length of the internal end of the cannula, i.e. at least the length of the membrane portion of the desired capsule, to lie within an acceptable, CSF filled space within the ventricle. The zero reference point for determining cannula insertion depth was the surface of the skin, as seen on the CT scan, and the target site was defined as the intended target of the internal tip (opening) of the inserting cannula. Two implant devices may be placed in one patient at a single procedure by placing one implant in each lateral ventricle. Future implantation sites may target the third ventricle, the aqueduct, and/or solid brain structures. The crent stereotactic guidance technique used CT imaging for reference, however MRI, stereotactic atlas coordinates, ultrasound or other guidance methods may also be appropriate. Following completion of data gathering for stereotactic placement of the implant(s), the patient was transferred to the operating room for the implantation procedure.

After establishing IV access and administering prophylactic antibiotics (currently, cefazolin sodium, 1 gram IV), the patient was positioned on the operating table in the semi-supine/seated position with the stereotactic head ring assembly secured to the table. The operative field was sterilely prepared and draped exposing the intended implantation site(s) (generally located in the paramedian, frontal region) and allowing for sterile placement and removal of the stereotactic arc system/manipulator to the frame base.

Local infiltration with 1.0% lidocaine was used for anesthesia of the skin and deeper scalp structures down to the periostium, and a 4–8 cm skin incision is made down to the skull at the calculated entry site(s) for the stereotactically guided insertion cannula (generally in the frontal region, in the parasagital plane 3 cm to the right or left of the midline) using electrocautery for homeostasis. A twist drill guided by the stereotactic arc system was then used to create a burr hole (generally 4 mm diameter) down to the level of the dura. The dura is sharply penetrated, and the insertion cannula/obturator assembly (CytoTherapeutics, Inc. implantation kit, specific for ventricular insertion) is mounted into the stereotaxic microdrive (CytoTherapeutics, Inc. custom fabrication, mounted in the guide block of the transverse arch slide of the arc system for use) and directed into the burr hole. Blood from the wound was excluded from the burr hole by applying the microdrive guide tube (CytoTherapeutics, Inc. custom fabrication) directly against the rim of the burr hole. The insertion cannula/obturator assembly were advanced manually to the preset depth stop on the microdrive, leaving the tip of the cannula at the target site. The obturator was then carefully withdrawn from the insertion cannula, taking care not to deflect the cannula with the top of the obturator. Appropriate position of the tip of the cannula within the ventricle was confirmed by a meniscus of cerebrospinal fluid (CSF) rising up within the clear insertion cannula after removal of the obturator. Samples of CSF were taken for preimplantation catacholamine, enkephalin, glucose, and protein levels and cell counts.

The encapsulated adrenal chromaffin cell graft (CytoTherapeutics, Inc. Cerecrib® R) was provided in a sterile, double envelope container, bathed in transport medium, and fully assembled including a tubular silicone tether. Prior to implantation through the insertion cannula and into the ventricle, the capsule was transferred to the insertion kit tray (CytoTherapeutics, Inc. implantation kit) where it was positioned in a location that allows the capsule to be maintained in transport medium while it is grossly examined for damage or major defects, and while the silicone tether was trimmed, adjusting its length to the pusher and removing the hemaclip that plugs its external stainless steel pusher (CytoTherapeutics, Inc. implantation kit, specific for insertion cannula and membrane capsule length) by inserting the small diameter wire portion of the pusher into the full length of the tether to stiffen the tether for passage through the cannula.

The Cerecrib capsule was handled completely by the silicone tether and the handle of the pusher as the membrane portion of the device was carefully introduced into the cannula. The capsule was advanced until the tip of the cannula positioned in the subarachnoid space (but not extending beyond the tip of the cannula positioned in the subarachnoid space (but not extending beyond the tip of the cannula). This placement was achieved by premeasuring the cannula and the capsule-tether-pusher assembly, and it assures that the membrane portion of the capsule is protected by the cannula for the entire time that it is being advanced into position. After the capsule was positioned manually within the cannula, the pusher is locked into position in the microdrive and used to hold the capsule in position in the ventricle (without advancing or withdrawing) while the cannula is completely withdrawn from over the capsule and pusher. The pusher was then removed from the capsule by sliding its wire portion out of the silicone tether. Using this method the final placement of the capsule was such that the entire membrane portion of the device lies entirely within an appropriate, CSF-containing region of the ventricle. The membrane capsule was anchored at its external end by a length of silicone tether that runs (generally) through a portion of the frontal lobe before it exits through the dura and the skull, leaving generally 5–10 cm of free tether material that was available for securing the device. The free end of the tether was then anchored to the outer table of the skull adjacent to the burr hole using a standard, maxillofacial miniplate and screws and completely covered with a 2 or 3 layer closure.

The patient was then transferred to the neurosurgical recovery area and followed for 12 hours postoperatively for potential hemorrhage complications with no special restrictions. Antibiotic prophylaxis was also continued for 24 hours following the implantation procedure.

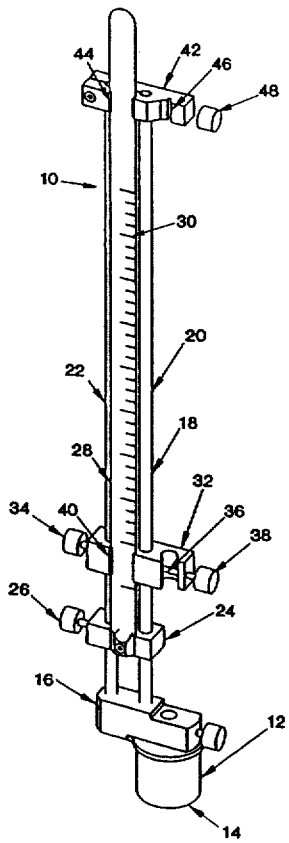

What is claimed is:

1. A method of inserting a surgical instrument into a portion of the central nervous system during stereotactic surgery comprising;

(a) attaching a surgical instrument to an instrument holding member of a microdrive apparatus wherein the microdrive apparatus is fixedly positioned relative to the central nervous system, said microdrive apparatus comprising a base member, an elongated guide member fixedly attached to the base member, an instrument holding member slidably attached to the guide member having a means for holding a surgical instrument, a stop member abutting and slidably attached to the guide member and disposed between the base member and the instrument holding member, said stop member being slidable on the guide member independent of the instrument holding member and a measuring member containing measuring indicia thereon fixedly attached to the stop member;

(b) placing the instrument holding member and the stop member together in an abutting relationship and adjusting them along the guide member so that the surgical instrument is disposed at a first predetermined position and thereafter temporarily fixedly attaching each such member to the guide member, (c) thereafter, releasing the stop member and sliding it along the guide member to a second predetermined position which second position corresponds to a position that is a predetermined distance from a predetermined target point in the central nervous system and then fixedly attaching the stop member to the guide member at such second predetermined position;

(d) thereafter, releasing the instrument holding member and sliding it along the guide member until it reaches a position where it abuts the stop member and is as a result a predetermined distance from a predetermined target point in the central nervous system, thereby inserting the surgical instrument into the central nervous system to a predetermined target point; and (e) thereafter, fixedly attaching the instrument holding member in the position described in step (d).

2. The method of claim 1, wherein the guide member comprises a pair of elongated rods spaced from each other a substantially equal distance along substantially their entire lengths.

3. The method of claim 1, wherein the apparatus additionally contains a second instrument holding member fixedly attached to the guide member.

4. The method of claim 1, wherein each of the stop member and the instrument holding member have means for temporarily prohibiting their abilities to slide along the guide member.

5. The method of claim 4, wherein the means for temporarily prohibiting sliding comprises a screw.

6. The method of claim 4, wherein the means for temporarily prohibiting sliding comprises bushings.

7. The method of claim 1, wherein the means for holding a surgical instrument is a notch in the holding member.

8. The method of claim 1, wherein the instrument holding member is slidably attached to the guide member in a manner which precludes movement in any direction other than along the axis of guide member.

9. The method of claim 1, wherein the base member comprises an instrument adapter member and a base stop member integral therewith.

10. The method of claim 9, wherein the instrument adapter member has a channel therethrough for passage of a surgical instrument.

11. The method of claim 1, wherein the portion of the central nervous system is a brain.

12. The method of claim 1, wherein the portion of the central nervous system is a spinal cord.

* * * * *

UNITED STATES PATENT AND TRADEMARK OFFICE
CERTIFICATE OF CORRECTION

PATENT NO. : 5,643,286
DATED : July 1, 1997
INVENTOR(S) : Warner et al.

It is certified that error appears in the above-identified patent and that said Letters Patent is hereby corrected as shown below:

In the Drawings:

Please replace the incorrect drawings for figures 2,3, and 4 with these corrected drawings for figures 2,3, and 4.

Signed and Sealed this

Fifth Day of May, 1998

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO. : 5,643,286
DATED : July 1, 1997
INVENTOR(S) : Warner et al.

It is certified that error appears in the above-identified patent and that said Letters Patent is hereby corrected as shown below:

The title page should be deleted to appear as per attached Title page.

Sheet 1 of 6 should be deleted to appear as per attached sheet 1 of 6.

Signed and Sealed this

Thirtieth Day of June, 1998

Attest:

BRUCE LEHMAN

Attesting Officer

Commissioner of Patents and Trademarks

United States Patent [19]

Warner et al.

[11] Patent Number: 5,643,286
[45] Date of Patent: Jul. 1, 1997

[54] MICRODRIVE FOR USE IN STEREOTACTIC SURGERY

[75] Inventors: Nicholas Warner, Belmont, Mass.; Moses Goddard, Tiverton; John Mills, Wakefield, both of R.I.

[73] Assignee: CytoTherapeutics, Inc., Providence, R.I.

[21] Appl. No.: 265,242

[22] Filed: Jun. 24, 1994

[51] Int. Cl.⁶ .............................. A61B 19/00; A61B 17/56
[52] U.S. Cl. ..................... 606/130; 606/96; 606/98; 606/167; 606/172; 604/116
[58] Field of Search ......................... 606/1, 130, 108, 606/96-98, 129, 167, 172; 128/749, 653.1, 653.2; 604/116

[56] References Cited

U.S. PATENT DOCUMENTS

| | | | |
|---|---|---|---|
| 3,223,087 | 12/1965 | Vladyka et al. | 606/129 |
| 3,817,249 | 6/1974 | Nicholson | 606/130 |
| 4,653,509 | 3/1987 | Oloff et al. | 606/130 X |
| 4,722,336 | 2/1988 | Kim et al. | 606/130 |
| 4,750,487 | 6/1988 | Zanetti | 606/130 |
| 4,875,478 | 10/1989 | Chen | 606/130 X |
| 4,940,061 | 7/1990 | Terwilleger | |
| 5,056,523 | 10/1991 | Hutchkiss, Jr. et al. | 606/130 X |
| 5,080,662 | 1/1992 | Paul | 606/130 |
| 5,154,723 | 10/1992 | Kubota et al. | 606/130 |
| 5,183,465 | 2/1993 | Xanthakos et al. | 606/172 X |
| 5,308,352 | 5/1994 | Koutrouvelis | 606/130 |

FOREIGN PATENT DOCUMENTS

| | | | |
|---|---|---|---|
| 2584601 | 1/1987 | France . | |
| 869842 | 3/1953 | Germany . | |
| 1055503 | 11/1983 | U.S.S.R. | 606/130 |

OTHER PUBLICATIONS

Bland et al., "A Direct-Drive, Non-Rotating Version of Ranck's Microdrive", *Physiology and Behavior*, vol. 24, May 16, 1979, pp. 395–397.

*Primary Examiner*—Danton D. DeMille
*Attorney, Agent, or Firm*—Ivor Elrifi; Bruce F. Jacobs

[57] ABSTRACT

The present invention is directed to microdrive apparatus useful in human stereotactic surgery. Such apparatus permits safe and accurate placement of a surgical instrument, such as a cannula, into a portion of the central nervous system, e.g. the brain and spinal cord, of a patient by simple mechanical operation.

12 Claims, 6 Drawing Sheets